(12) United States Patent
Farrell (10) Patent No.: US 9,433,583 B2
(45) Date of Patent: Sep. 6, 2016

(54) COLON VITAMIN

(76) Inventor: Frank J. Farrell, San Francisco, CA (US)

( * ) Notice: Subject to any disclaimer, the term of this patent is extended or adjusted under 35 U.S.C. 154(b) by 988 days.

(21) Appl. No.: 13/453,228

(22) Filed: Apr. 23, 2012

(65) Prior Publication Data

US 2012/0269869 A1    Oct. 25, 2012

Related U.S. Application Data (60) Provisional application No. 61/478,345, filed on Apr. 22, 2011.

(51) Int. Cl.
| | | |
|---|---|---|
| *A61K 33/06* | (2006.01) | |
| *A61K 31/592* | (2006.01) | |
| *A61K 9/28* | (2006.01) | |
| *A61K 31/59* | (2006.01) | |
| *A61K 9/48* | (2006.01) | |
| *A61K 9/50* | (2006.01) | |

(52) U.S. Cl.
CPC ........... *A61K 9/2846* (2013.01); *A61K 9/4808* (2013.01); *A61K 9/5026* (2013.01); *A61K 9/5084* (2013.01); *A61K 31/59* (2013.01); *A61K 33/06* (2013.01)

(58) Field of Classification Search
CPC .. A61K 9/4808; A61K 33/06; A61K 31/592; A61K 9/2846; A61K 9/5084
USPC ........ 424/400, 682, 468, 729, 702; 514/167, 514/963
See application file for complete search history.

(56) References Cited

U.S. PATENT DOCUMENTS

| | | |
|---|---|---|
| 4,752,479 A | 6/1988 | Briggs |
| 4,845,123 A | 7/1989 | Walaszek |
| 5,698,222 A | 12/1997 | Mazer |
| 6,231,888 B1 | 5/2001 | Lerner |
| 6,245,360 B1 | 6/2001 | Markowitz |
| 6,248,362 B1 | 6/2001 | Tominaga |
| 6,251,439 B1 | 6/2001 | Baron |
| 6,395,279 B1 | 5/2002 | Empie |
| 6,436,446 B1 | 8/2002 | Forusz |
| 6,488,966 B2 | 12/2002 | Baron |
| 6,558,711 B1 | 5/2003 | Baron |
| 6,562,378 B1 | 5/2003 | Chandra |
| 6,579,544 B1 | 6/2003 | Rosenberg |
| 6,646,013 B1 | 11/2003 | Barker |
| 6,761,912 B2 | 7/2004 | Forusz |
| 6,900,240 B2 | 5/2005 | Empie |
| 6,949,258 B2 | 9/2005 | Zhang |
| 7,601,699 B2 | 10/2009 | Eilertsen |
| 2004/0022845 A1 | 2/2004 | Zhang |
| 2005/0260283 A1 | 11/2005 | Nijhawan |
| 2006/0210646 A1 | 9/2006 | Oku |
| 2006/0251722 A1 | 11/2006 | Bandak |
| 2007/0292493 A1 | 12/2007 | Brierre |
| 2008/0020018 A1 | 1/2008 | Moodley |
| 2008/0113031 A1 | 5/2008 | Moodley |
| 2008/0193531 A1 | 8/2008 | Hermelin |
| 2009/0004297 A1 | 1/2009 | Ranganathan |
| 2010/0009948 A1 | 1/2010 | Nelson |
| 2010/0120727 A1 | 5/2010 | Xu |
| 2010/0255118 A1 | 10/2010 | Kanzer |

FOREIGN PATENT DOCUMENTS

| | | |
|---|---|---|
| CN | 1579233 | 2/2005 |
| CN | 1961957 | 5/2007 |
| CN | 101336950 | 1/2009 |
| CN | 101675804 | 3/2010 |
| JP | H0413629 | 1/1992 |
| WO | WO 03007916 A1 * | 1/2003 |
| WO | WO2011024208 | 3/2011 |

OTHER PUBLICATIONS

Grau et al. Vitamin D, Calcium Supplementation, and Colorectal Adenomas: Results of a Randomized Trial; Journal of the National Cancer Institute, vol. 95, No. 23, Dec. 3, 2003.*
Röhm Pharma Polymers, Practical Course in Film Coating of Pharmaceutical Dosage Forms with Eudragit, Degussa 2000.*
Giovannucci et al. Multivitamin Use, Folate and Colon Cancer in Women in the Nurses' Health Study, Ann Intern Med. 1998;129(7), abstract.*

* cited by examiner

*Primary Examiner* — Michael G Hartley
*Assistant Examiner* — Nabila Ebrahim
(74) *Attorney, Agent, or Firm* — Staniford Tomita LLP (57) ABSTRACT

A colon vitamin includes ingredients that are delivered to different regions of the digestive tract. A first group of ingredients which can include: vitamin D, folic acid, vitamin B2, vitamin B6, beta-carotene, selenium, curcumin, green tea extract, and a portion of the calcium serving can be in a first delivery mechanism that releases these ingredients in the stomach. A second delivery mechanism is used to deliver elemental calcium intact through the stomach and small intestine to the large intestine. The delivery of the ingredients to specific areas of the digestive tract reduces the risk of colorectal adenomatous polyps and colorectal cancers.

10 Claims, 6 Drawing Sheets

COLON VITAMIN

CROSS REFERENCE TO RELATED APPLICATIONS

This application claims priority to U.S. Provisional Patent Application No. 61/478,345, "Colon Vitamin" filed Apr. 22, 2011, the contents of which are hereby incorporated by reference.

BACKGROUND

Colon and rectal cancers are leading causes of cancer-related mortality. Colon and rectal cancer are often collectively referred to as colorectal cancer. Colorectal cancer is the fourth most common cancer in the world and it ranks second in terms of cancer deaths in the United States for men, and third for women. In the United States, 55,000 people die of colorectal cancer each year. The incidence of colorectal cancer is similar for men and women except in high-incidence areas where rates for men exceed women by 20%. In addition, the incidence of rectal cancer is 1.5-2 times as likely in men as in women. Although the epidemiology is somewhat different for colon and rectal cancer, data suggest that dietary risk factors are similar.

Colorectal cancer usually develops slowly and progresses through stages described as the adenoma-carcinoma sequence. The initial event in this sequence is the development of aberrant crypt foci (ACF). Subsequently, an adenomatous polyp arises and over time develops into an early malignancy. This early malignancy sequence can take 10-15 years. The development of an adenomatous polyp can be a precursor for colorectal cancer.

The majority of sporadic colon and rectal cancers can occur in adenomas secondary to dysregulation of proto-oncogenes, loss of tumor suppressor gene function, and DNA mismatch repair. These defects result in more localized disease despite the widespread exposure of the colon to various environmental factors, whereas patients who inherit cancer syndromes tend to develop numerous polyps. The progression of aberrant crypt foci (ACF) to polyps is associated with up-regulation of COX-2, inducible NO synthase (INOS) and hydroxy methyl glutaryl CoA reductase (HMG-CoA reductase).

Despite improvement in screening practices, surgical techniques, and adjuvant therapy, the mortality rate from colorectal cancer has decreased by only 1.8% per year over the last 15 years. Therefore, primary prevention of colorectal cancer is an important goal. What is needed is a dietary supplement which can provide ingredients to the body to help prevent colorectal adenomatous polyps and colorectal cancers by maintaining the body's proper tumor suppressor gene and DNA mismatch repair functionality.

SUMMARY OF THE INVENTION

The present invention is directed towards a colon vitamin which can be taken orally by a patient for reducing the risk of colorectal adenomatous polyps and colorectal cancers. Embodiments of the colon vitamin can include various ingredients including calcium, vitamin D, folate, vitamin B2, vitamin B6, beta-carotene, selenium, curcumin and green tea extract (GTE). The colon vitamin can have a delivery mechanism which releases some of the ingredients into the small intestines while other ingredients remain encapsulated and are only released in the large intestine portion of the digestive tract (e.g. calcium). When calcium is released into the large intestine, the calcium binds fatty acids and bile acids in the intestinal lumen thus inhibiting their cytotoxic activity.

In a preferred embodiment, the ingredients of the colon vitamin can be enclosed in caplet and in other embodiments, the colon vitamin can be enclosed in a relatively stable shell known as a "capsule." The colon vitamin caplet or capsule can be taken orally by swallowing with water. The caplet can have a polymer coating that surrounds the colon vitamin pill ingredients which can be in a dry, powdered form or miniature pellets. The polymer can be a poly(meth)acrylate which is soluble in the body's digestive fluids and release the surrounded ingredients when exposed to digestive fluids having specific pH levels. Similarly, a hard-shelled capsule can be used to contain these ingredients. The capsule shell can be made from aqueous solutions of gelling agents like animal protein such as gelatin or plant polysaccharides or their derivatives like carrageenans and modified forms of starch and cellulose. Other ingredients can be added to the gelling agent solution of the capsule like plasticizers such as glycerin and/or sorbitol, coloring agents, preservatives, disintegrants, lubricants and other materials.

The caplet or capsule structure can be formulated to dissolve and release the colon vitamin pill ingredients at specific locations in the digestive tract of the body. The colon vitamin ingredient release mechanism can be based upon time within the digestive tract, exposure to digestive fluids having specific pH levels or exposure to or may break down to release the calcium when exposed to digestive fluids that only exist in the large intestine. For example, the protective matrix may release the calcium in response to exposure to specific types of bacteria that exist in the large intestine. The large intestine houses over 700 species of bacteria.

In an embodiment the colon vitamin pill can be a single pill that includes: vitamin D, folate, vitamin B2, vitamin B6, beta-carotene, selenium, curcumin, green tea extract (GTE) and calcium. It may be desirable to have the vitamin D, folate, vitamin B2, vitamin B6, beta-carotene, selenium, curcumin, GTE, and a portion of the calcium serving pass through the stomach in a protected state and the release these ingredients to the patient's small intestine. It may also be desirable to have the remaining portion of the calcium serving pass through the stomach and small intestine in a protected state. The colon vitamin may include a mechanism to delay the release of the calcium so that it is only delivered to the large intestine.

In order to accomplish this, the vitamin D, folate, vitamin B2, vitamin B6, beta-carotene, selenium, curcumin, GTE, and a portion of the calcium serving may be contained in a first structure that releases these ingredients in the patient's small intestine. However, the remaining portion of the calcium serving may be contained in a second structure that is different than the first structure. After the first structure releases the other ingredients in the small intestine, the second structure may continue to protect the calcium and may only release the calcium after the second structure has reached the large intestine. In order to delay the release of the ingredients in the stomach, the first structure may have a protective matrix that only releases the ingredients after passing through the stomach. The second capsule can have a protective matrix to allow it to pass intact through the stomach and the small intestine but release the calcium in the large intestine. By only releasing the calcium in the large intestine, the calcium can bind fatty acids and bile acids to neutralize their cytotoxicity and help to reduce the risk of colorectal cancers.

In another embodiment, the colon vitamin can be two separate capsules that are taken together. The first capsule can contain: vitamin D, folate, vitamin B2, vitamin B6, beta-carotene, selenium, curcumin, GTE, and a portion of the calcium serving which are released together in the small intestine and the second capsule can contain the remaining portion of calcium which is released in the large intestine. The colon vitamin can have several different embodiments. For example, the first and second pills can be physically separate structures that can be ingested together.

The quantity of ingredients can be sufficient for a full day so that a normal consumer would ingest a single colon vitamin serving on a once-a-day dosage schedule. In other embodiments, the colon vitamin may have smaller quantities of ingredients. For example, an embodiment of the colon vitamin can be half the normal recommended daily dosage. In this embodiment, the consumer may ingest a colon vitamin on a twice-a-day dosage schedule. This smaller dosage embodiment may have a smaller colon vitamin pill size which is easier to swallow and the body may be able to absorb the ingredients more easily if the colon vitamins are consumed at two different times during the day.

DETAILED DESCRIPTION

A colon vitamin is consumed by users to prevent colorectal adenomatous polyps and colorectal cancer. In a preferred embodiment, the ingredients can be enclosed in a relatively stable tablet allowing them to be taken orally by swallowing with water. A tablet can be used to contain the colon vitamin ingredients which can be in a dry, powdered form, miniature pellets or any other suitable form.

The colon vitamin can have a tablet structure that can be formulated to dissolve and release the colon vitamin pill ingredients at specific locations in the body. For example, the colon vitamin may be configured to deliver a first delivery portion which includes a first set of ingredients released in the small intestines and a second delivery portion which includes a second set of ingredients released in the large intestines or colon.

In order to release different ingredients in different locations, the colon vitamin may include different delivery mechanisms that can release the ingredients when the colon vitamin is in the targeted portions of the body. Various ingredient release mechanisms can be used to release the ingredients into the body. These ingredient release mechanisms can be based upon various factors including: chemical environment within the body and time. In an embodiment, the colon vitamin can have a caplet structure that has an outer protective polymer layer that can release the ingredients in specific locations of the body. In an embodiment, the caplet can have a protective layer made of poly(meth) acrylate.

In other embodiments, the colon vitamin may be in the form of a capsule having a shell that can be made from aqueous solutions of gelling agents like animal protein mainly gelatin or plant polysaccharides or their derivatives like carrageenans and modified forms of starch and cellulose. Other ingredients can be added to the gelling agent solution like plasticizers such as glycerine and/or sobitol, coloring agents, preservatives, disintegrants, lubricants and other materials.

Humans have upper and lower gastrointestinal tracts. The upper gastrointestinal tract includes the mouth, esophagus, stomach, and the proximal portion of the small intestines. The lower gastrointestinal tract includes the remaining small intestines and colon including the rectum. The time taken for the colon vitamin to transit through the gastrointestinal tract varies depending on many factors. However, it may take about 2.5 to 3 hours after a meal for 50% of stomach contents to empty into the intestines and total emptying of the stomach can take about 4 to 5 hours. Subsequently, emptying about 50% of the small intestine can take about 2.5 to 3 hours. Finally, transit through the large intestines and colon can take about 30 to 40 hours. Thus, in order to release a first group of ingredients in the stomach and small intestines, the colon vitamin can release the first group of ingredients at about 0.5 to 2 hours after being swallowed by the patient. Then, the colon vitamin can release the second group of ingredients after about 8 to 20 hours after being swallowed.

The time-release mechanism can be formulated so that selected ingredients embedded within a matrix of insoluble substances such that the dissolving drug must find its way out through the holes in the matrix. Some ingredients are enclosed in polymer-based structure with small holes on one side and a porous membrane on the other side. Gastric fluids that include gastric acid can enter the structure through the porous membrane and push the encapsulated ingredients out of the structure through the holes. In time, the entire contents of the structure can be released into the patient while the polymer structure remains intact. This polymer structure can be excreted from the body through normal digestion.

In some embodiments, the ingredients of the colon vitamin can be dissolved into an expandable gel matrix which is used to form the colon vitamin. The gel matrix can hold the ingredients of the vitamin which prevents the release until the vitamin reaches the target area. When the matrix of the colon vitamin is swallowed, it enters the digestive tract and is exposed to digestive fluids. The matrix can physically swell when exposed to specific digestive fluids and in the expanded state the matrix can form a gel which releases the dissolved ingredients. In the gel form, the ingredients can exit the colon vitamin through the outer surface of the gel and be absorbed by the body.

Figure 1:
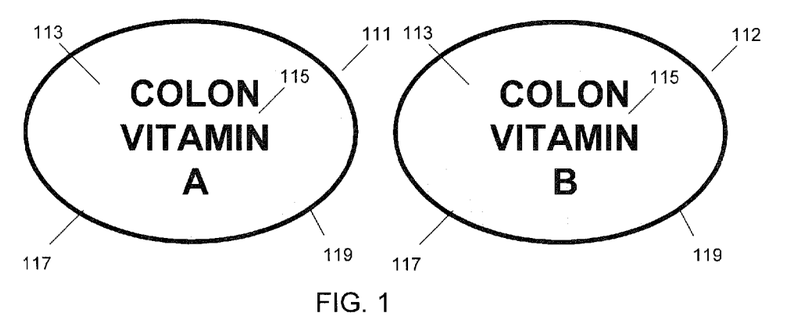
FIG. 1 illustrates a top view of a first microencapsulated colon vitamin and a second microencapsulated colon vitamin.
Figures 2, 3:
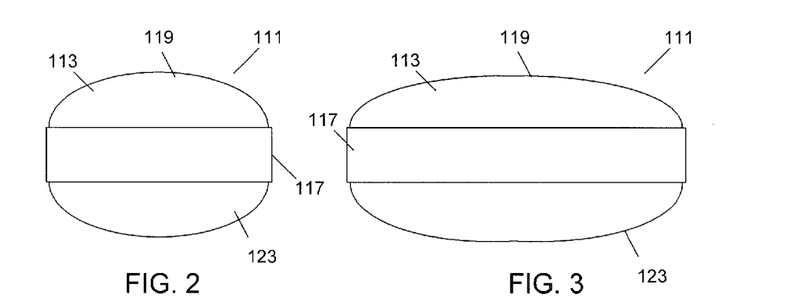
FIGS. 2 and 3 illustrate side views of a colon vitamin caplet.
Figure 4:
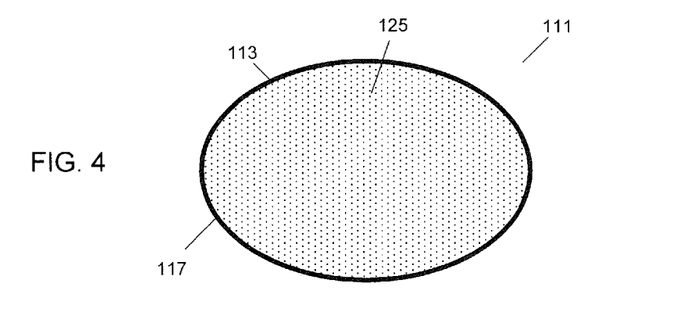
FIG. 4 illustrates a cross section side view of a colon vitamin.

With reference to FIGS. 1-4, in an embodiment, the colon vitamin pill can be in the form of a caplet 111. FIG. 1 illustrates a top view of an embodiment of the colon vitamin in two caplet form, FIGS. 2 and 3 illustrate side views of the colon vitamin 111 and FIG. 4 illustrates a cross section view of the colon vitamin 111. With reference to FIG. 1, the colon vitamin can be in the form of two caplets 111, 112 which can each contain different ingredients. Each caplet 111, 112 can be distinctly marked 115 to distinguish them. The caplets can include an exterior layer 119 that surrounds the compressed ingredients which can be contained within a polymer matrix. FIGS. 2 and 3 illustrates side views of the caplet 111 having a lower side 123 and upper side 119 and a middle section 117 that can have vertical walls. FIG. 4 illustrates a cross sectional view of the colon vitamin caplet 111 which can contain a mixture of active ingredients 125 and excipients usually in powder form which can be pressed or compacted from a powder with a polymer into a solid dose. The excipients can include diluents, binders or granulating agents, glidants (flow aids) and lubricants to ensure efficient tabletting, disintegrants to promote tablet break-up in the digestive tract, etc. The polymer 113 can be a poly(meth) acrylate can that controls the release of the active ingredients. In the compressed caplet form, the colon vitamin can be stamped with symbols, letters, and numbers 115, which enable them to be identified.

In an embodiment, the colon vitamin in caplet form can be made with a caplet press machine having a die, an upper punch and a lower punch. The die can be the shape of the perimeter of the caplet 117 and the upper and lower punch can have the shape of the upper surface 119 and the lower surface 121 of the caplet respectively. The lower punch can be position at a lower portion of the die and the die can be filled with the ingredients of the colon vitamin in powder form and a polymer. Once the die is filled with the proper quantity of ingredients, the upper punch can then be lowered into the caplet die and the powder can be uniaxially compressed to bind the ingredients within the polymer matrix. The porosity of the caplet can be about 5 to 20%. The compression can take place in one stage or two stages. If two stage compression is used, a first compression can be a pre-compression or tamping compression which is followed by the second main compression. The upper punch and/or lower punch can include symbols, letters, and numbers 115 which can be marked on the caplet 111 and can be used to identify the caplet 111. The upper punch is then pulled up and out of the die and the caplet 111 can be ejected from the die by lifting the lower punch until its upper surface is flush with the top face of the die. This process can be automatically repeated for each caplet 111 manufactured.

In an embodiment, the polymer matrix can include a pH based release mechanism surrounding the ingredients and controlling the release location in the digestive system based upon the ambient pH level. In an embodiment, the polymer matrix can be stable at a highly acidic pH environment such as the pH levels found in the stomach. Once the colon vitamin passes through the stomach, it is exposed to a less acidic and more basic pH level. For example, a first polymer matrix can protect a first group of ingredients in an acidic environment of 1.0 to 5.0 pH and release the first group of ingredients in a less acidic environment of the small intestine with a pH of about 6.0 to 7.0. A second polymer matrix may also not dissolve or release a second group of ingredients in the acidic juices of the stomach. The second polymer matrix may pass through the stomach and small intestines and may dissolve and release the second group of ingredients in an alkaline environment having a pH level of equal to or greater than 7.0 in the large intestine.

After the caplet 111 is formed by the press, a coating can be applied to the caplet forming an outer protective layer. The coating 113 can be useful to extend the shelf-life of components that are sensitive to moisture or oxidation. In different embodiments, coating pans or automatic coaters can be used to form the coating layers 113 on the caplets 111.

The ingredients of the colon pill and delivery mechanism can be combined in various different ways. In an embodiment, the first group of ingredients may be pressed into a caplet alone and not be mixed with the polymer matrix materials. A coating can be applied over the first group of ingredients. The coating layer surrounding the caplet can be configured to release the ingredients in the pH environment of 6.0-7.0 in the small intestine or have a time release mechanism which can dissolve quickly in 6.0-7.0 pH to release the first group of ingredients in the small intestine. Similarly, the second caplet can have an enteric coating which is resistant to stomach acid. The enteric coating can remain intact as it passes through the stomach and can dissolve and release the calcium in the large intestines with a pH equal to or greater than 7.0.

Figure 5:
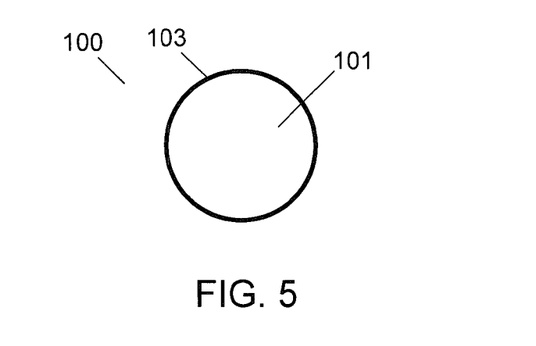
FIGS. 5 and 6 illustrate cross section side views of embodiments of colon vitamin ingredients.

With reference to FIGS. 5 and 6, micro-encapsulation is another technology that can be used by the inventive colon vitamin to produce specific ingredient deliveries. With reference to FIG. 5, the colon vitamin ingredients can be in the form of small particles 101 in a powder form that are surrounded by a coating 103 that can be a small sphere that provides a uniform protective wall around the colon vitamin ingredients 101. The ingredients 101 inside the microcapsule 103 can be referred to as the core, internal phase, or fill and the wall 103 can be called a shell, coating or membrane. The microcapsules 100 can have diameters between a few micrometers and a few millimeters. The wall 103 can be designed to release the ingredients 101 in specific conditions such as a predetermined elapsed time in the digestive system or in specific chemical environments such as pH levels. Different ingredients 101 can be surrounded by the microcapsule 103 and each of these ingredients 101 can be released within a patient under the predetermined release conditions. For example, the microcapsule 103 can be designed to deliver the ingredients 101 to the small intestine.

Figure 6:
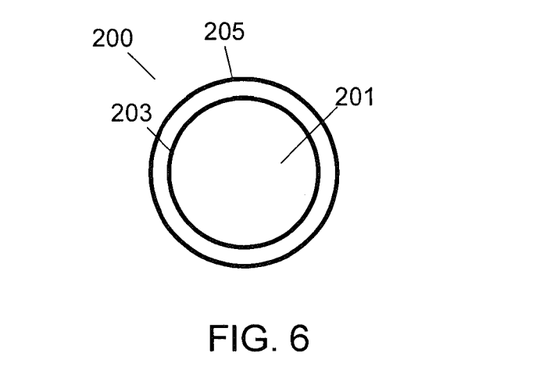

With reference to FIG. 6, different walls 203 can be used to deliver ingredients 201 to different portions of the patient's digestive tract. For example, in another embodiment of micro-encapsulation, the wall 203 can be coated in multiple layers 204, 205 around the ingredients 201 which can again be small particles. The wall materials 204, 205 can be layered with insoluble substances to form a microsphere. This multi-layered configuration can provide a different delivery location for the ingredients 201. For example, the microcapsule 203 can be designed to deliver the ingredients 201 to the large intestine. Different microcapsules can be used for the different ingredients and different coatings can be applied depending upon the target area of the digestive system for each ingredient.

Figure 7:
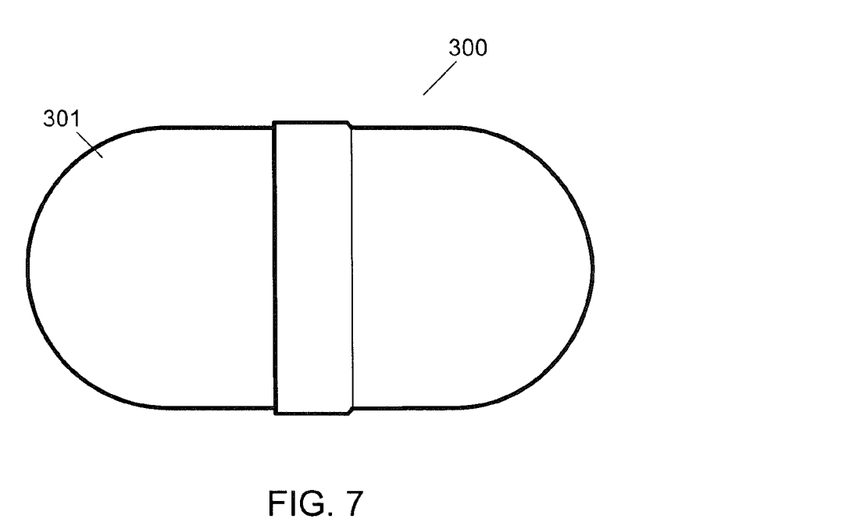
FIGS. 7 illustrates a side view of an embodiment of a colon vitamin capsule.
Figure 8:
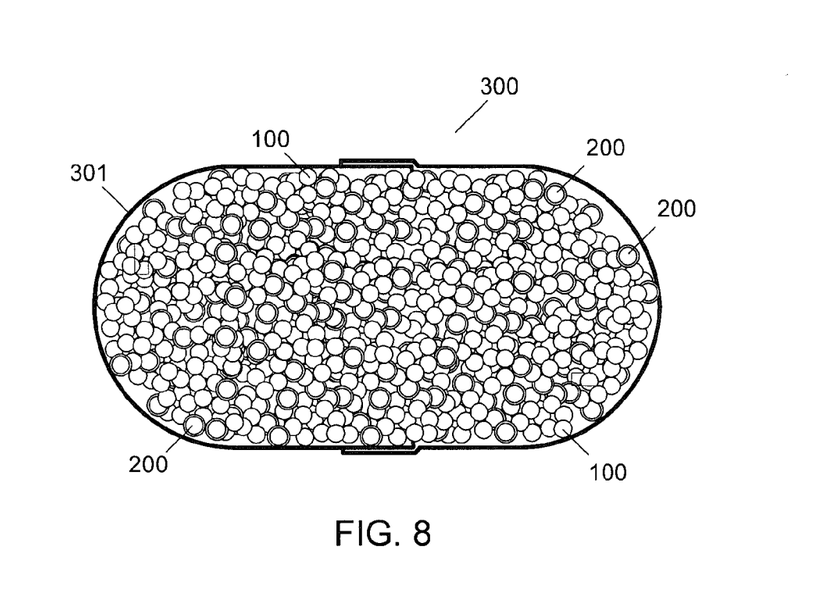
FIGS. 8-13 illustrate cross section side views of embodiments of colon vitamins having multiple delivery mechanism capsules.

FIG. 7 illustrates a side view of the two piece capsule 300 and FIG. 8 illustrates a cross section view of the two piece capsule 300 filled with the microsphere structures 100, 200. With reference to FIG. 4, the microsphere structures 100, 200 can be placed within a two-piece capsule 300 that can easily be swallowed by a patient. The quantities of the different microsphere structures 100, 200 can depend upon the dosages of each ingredient contained in the colon vitamin. The two-piece capsule 300 can be made of gelatin which can dissolve soon after ingestion by the patient. The microsphere structures 100, 200 will then travel through the patient independently and each microsphere structure 100, 200 will deliver its core ingredients to the predetermined locations digestive tract.

Figure 9:
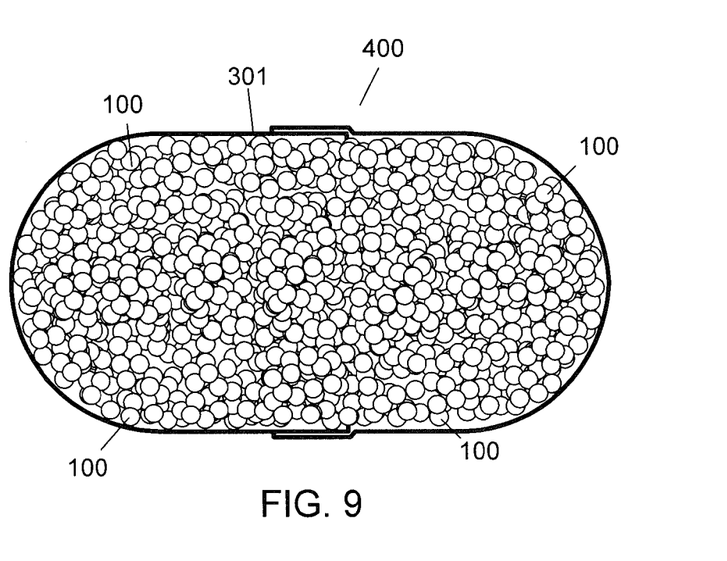
Figure 10:
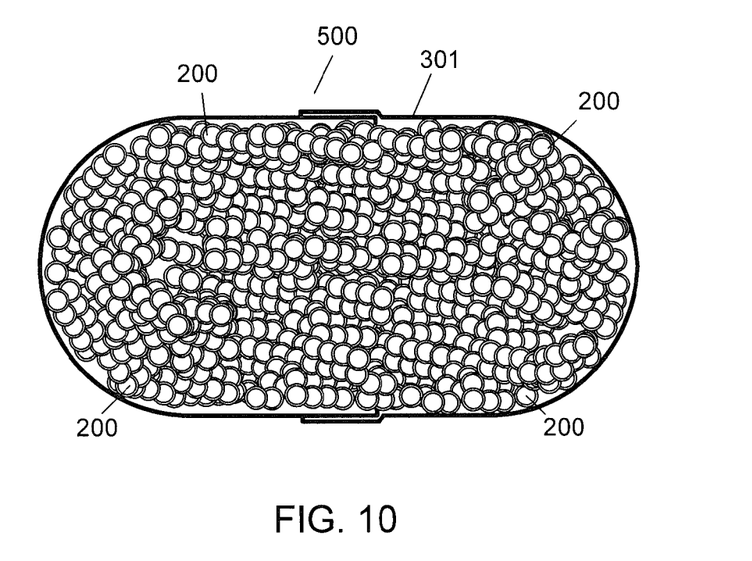

In other embodiments, the different microsphere structures can be separated into different capsules. With reference to FIG. 9, a first capsule 400 can contain only a first type of microsphere 100 containing ingredients for delivery to the small intestine. With reference to FIG. 10, a second capsule 500 can contain only a second type of microsphere 200 containing ingredients for delivery to the large intestine. Because the microsphere walls have the delivery mechanism, the first capsule 400 and the second capsule 500 can be made of a gelatin which can dissolve soon after ingestion by the patient.

In order for the ingredients to be released, the wall of the first microstructure 100 and the second microstructure 200 must be ruptured. As discussed above, the microstructure 100 is designed to release its ingredients in the stomach or small intestine while the microstructure 200 is designed to release its ingredients in the large intestine. Thus, the first microstructure 100 and the second microstructure 200 have different structures which rupture under different conditions. The ingredients may be released by melting or dissolving the wall under particular conditions. For example, the ambient pH level can cause the wall of the microstructure 100, 200 to dissolve in the case of an enteric drug coating. Alternatively, the wall can be broken by solvent action, enzyme attack, chemical reaction, hydrolysis, or slow disintegration.

In other embodiments, the described microencapsulation can be used to slow the release of the colon vitamin ingredients into the body. This may permit one controlled slow release dosage of ingredients. In some cases the desired release rate of ingredients is constant over a period of time. The microcapsules can deliver a predetermined amount of ingredients per minute or hour during the period of their effectiveness. Because the ingredients may remain in a specific location for an estimated period of time, the different delivery times can still result in the ingredients being delivered to the specified target portion of the digestive tract.

In other embodiments, the microencapsulation can be designed to release the ingredients based upon pH level. As the colon vitamin passes through the gastrointestinal tract the acidity or pH level changes and by using a pH based microencapsulation release mechanism, the ingredients can be delivered to the proper locations. In the mouth, pharynx, and esophagus, pH is typically about 6.8, very weakly acidic. Saliva controls pH in this region of the digestive tract. Most digestive enzymes are sensitive to pH and will denature in a high or low pH environment. The stomach can have a high acidity of about 1-5 pH. In the small intestines, the duodenum provides critical pH balancing to activate digestive enzymes. The liver secretes bile into the duodenum to neutralize the acidic conditions from the stomach, and the pancreatic duct empties into the duodenum, adding bicarbonate to neutralize the acid, thus creating a neutral environment. The mucosal tissue of the small intestines is alkaline and can have a pH of about 6.0-7.0 and the large intestines is also alkaline with a pH of more than 7.0.

In an embodiment, the colon vitamin can include a pH based microencapsulation protective barrier surrounding each of the ingredients and the release mechanism can control the location in the digestive system where the ingredients are released based upon the ambient pH level. In an embodiment, the protective barrier can be stable at a highly acidic pH environment such as the pH levels found in the stomach. Once the colon vitamin passes through the stomach, it is exposed to a less acidic and more basic pH level. For example, the outer layer of the protective barrier may not dissolve in the acidic juices of the stomach, pH 1-5, but may dissolve in the alkaline pH 6.0-7.0 environment present in the small intestine to expose an inner layer protective barrier. This inner protective barrier may not dissolve in the pH of the small intestines but may dissolve to release ingredients in the more alkaline pH of the large intestine. Materials used for protective coatings include fatty acids, waxes, shellac, plastics, plant fiber and other suitable materials.

In an embodiment the colon vitamin pills may include: vitamin D, folate, vitamin B2, vitamin B6, beta-carotene, selenium, curcumin, green tea extract (GTE) and calcium. It may be desirable to release the vitamin D, folate, vitamin B2, vitamin B6, beta-carotene, selenium, curcumin, GTE, and a portion of the calcium into the patient's stomach or small intestine but also have the remaining portion of the calcium released in the large intestine. In order to accomplish this, the vitamin D, folate, vitamin B2, vitamin B6, beta-carotene, selenium and calcium may be contained in a first tablet that dissolves in the patient's stomach or small intestine. In contrast to the other ingredients, the calcium may be placed in a second different protective structure that may not release the calcium until it has passed through the small intestine and has reached the large intestine. In an embodiment, each of these ingredients can be placed within a microencapsulation as described above which will deliver.

Figure 11:
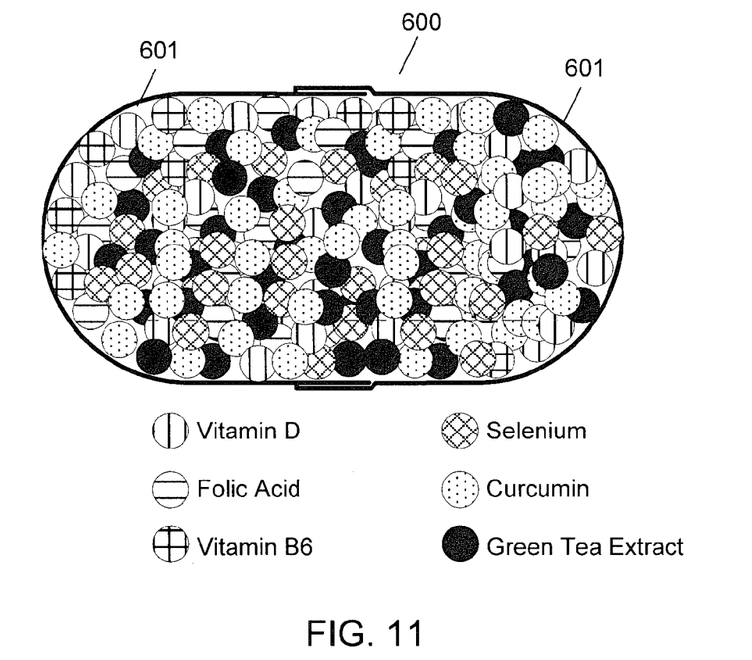
Figure 12:
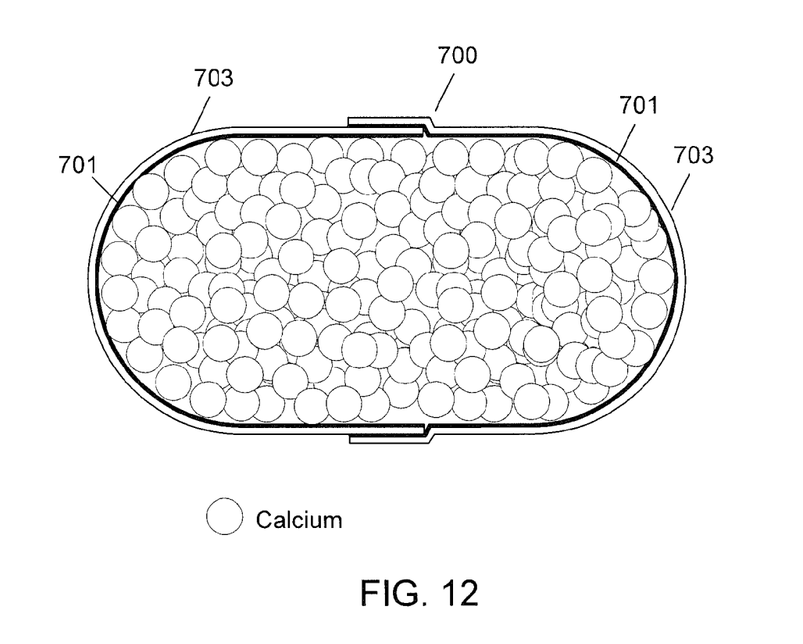

In other embodiments, the ingredients may not be microencapsulated and the outer capsule may provide the location specific delivery mechanism for the ingredients. With reference to FIG. 11, a first capsule 600 having a wall or shell 601 that can include a timed release or a pH based delivery mechanism which delivers the ingredients to the stomach or small intestine of the patient. The ingredients within the capsule can include: vitamin D, folic acid, vitamin B2, vitamin B6, beta-carotene, selenium, curcumin, green tea extract, and a portion of the calcium. These ingredients can be mixed and spaced within the capsule 600. With reference to FIG. 12, a second capsule 700 can include a different timed release and/or pH based delivery mechanism than the first capsule 600. The second capsule 700 may surround calcium alone or in combination with other ingredients. In order to delay the release of the calcium, the second capsule 700 can include a protective matrix having an inner shell 701 and an outer shell 703. This inner shell 701 and outer shell 703 combination allow the calcium to pass intact through the stomach and the small intestine to the large intestine where the calcium is released in the large intestine.

The protective matrix may simply delay the release of the calcium based upon time and exposure to GI fluids or may break down to release the calcium when exposed to fluids that are only in the large intestine. Alternatively, the calcium can be surrounded by a multiple layer protective barrier having an inner layer 701 and an outer layer 703. The outer layer 703 may resist the high acidity of the stomach but dissolve in the more alkaline environment when it reaches the small intestine. Once the outer layer 703 has been removed, the inner layer 701 can still prevent the calcium from being released in the small intestines. The inner layer 701 may dissolve in a pH of more than 7.0 which can cause the colon vitamin to release the calcium in the large intestine. In other embodiments, other mechanisms can be used to prevent the calcium from being released until the colon vitamin reaches the large intestine.

Figure 13:
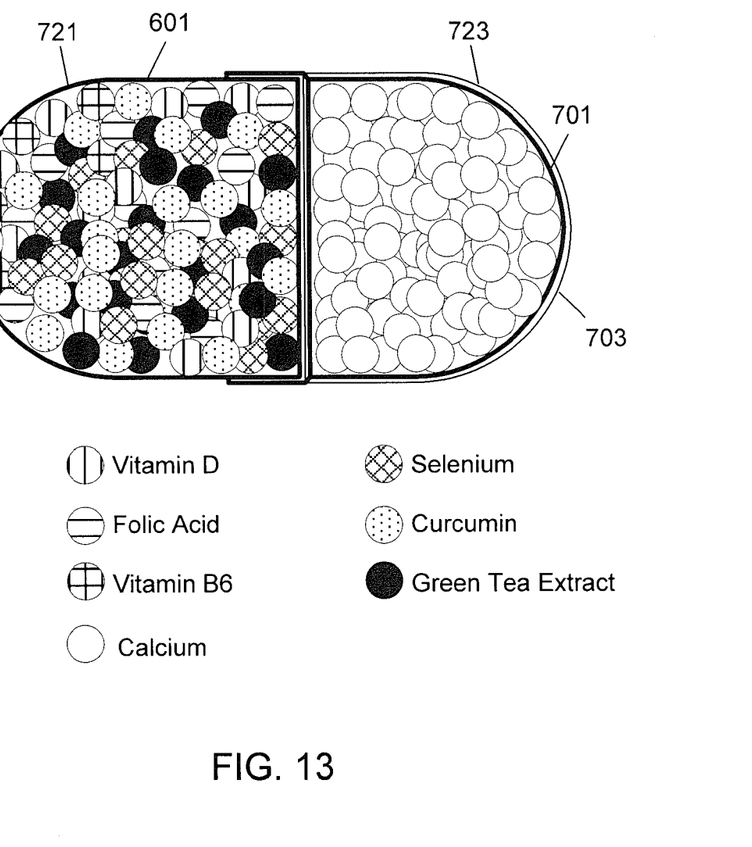

The colon vitamin can have various different configurations and can be taken at a suggested rate of one pill per day or multiple pills per day. In an embodiment, all of the ingredients can be in a single pill. As discussed above with reference to FIGS. 11 and 12, the colon vitamin can include a first capsule 600 and a second capsule 700 that can be separate pills that are taken at the same or at different times by the patient. With reference to FIG. 13, in an embodiment, a first capsule 701 and a second capsule 710 can be physically connected so that the patient only needs to ingest a single colon vitamin. However, the first capsule 721 and the second capsule 723 can effectively function as two separate capsules after ingestion. The release mechanisms can be time or pH based as described above. The first capsule 721 can have a first release mechanism for delivering the ingredients to the stomach or small intestine. The first release mechanism can be the wall or shell 601 described above with reference to FIG. 11. The second capsule 710 can have a second release mechanism which releases the calcium into the large intestine and can have the inner wall 701 and outer wall 703 mechanism described above with reference to FIG. 12.

Chemoprevention involves the use of natural or synthetic agents to reverse, suppress, or prevent the occurrence of cancer or the events leading to precancerous lesions. An ideal agent to prevent colorectal neoplasia must target a step in carcinogenesis, have efficacy against colorectal cancer, be cost effective, have easy administration, and be safe with a favorable side-effect profile. Certain micronutrients and antioxidants have been shown to decrease the incidence of colonic adenomatous polyps. These micronutrients and antioxidants which can be ingredients of the colon vitamin include calcium, vitamin D, folic acid (folate), vitamin B2, vitamin B6, beta-carotene, selenium, curcumin and green tea extract (GTE).

Calcium

Calcium can reduce the risk of colorectal cancer by binding to bile acids and fatty acids in the gastrointestinal tract to form insoluble complexes known as calcium soaps. This transformation reduces the ability of the acids or their metabolites to damage cells in the lining of the colon and stimulates cell proliferation to repair the damage. Calcium may also act directly to reduce cell proliferation in the lining of the colon or cause proliferating colon cells to undergo differentiation, which, in turn, leads to a reduction in cell proliferation. Calcium also may improve signaling within cells and cause cancer cells to differentiate or die. Calcium may also reduce pathological cytokinetic crypt activity. Calcium can be absorbed passively in the large intestines by diffusing through spaces between intestine cells. Calcium can also be absorbed actively through intestinal cells by binding to a transport protein known as calbindin. The production of calbindin is dependent on vitamin D which is also an ingredient of the colon vitamin. Thus, the combination of calcium and vitamin D improves the absorption of calcium.

A daily intake of one gram of dietary calcium might have a moderate protective effect on the development of colorectal adenomatous polyps. However, calcium should not be taken in excess of 5 grams a day, or 3 grams a day in people with existing kidney problems as this can lead to several harmful side effects including: kidney stones, hypercalcemia and kidney failure. In addition, excessive consumption of milk which is high in calcium and some types of antacids, especially antacids containing calcium carbonate or sodium bicarbonate (baking soda), over a long period of time can cause milk-alkali syndrome, a condition that can also lead to calcium deposits in the kidneys and other tissues and kidney failure.

As discussed above, the elemental calcium can be delivered intact to the large intestine rather than passing through the stomach and small intestine where it can be absorbed prior to reaching the large intestine. Calcium can act to reduce cell proliferation and reduce the potential promoting effects of bile acids and free fatty acids by conversion of these into insoluble calcium soaps in the large intestine. By delivering a portion of the calcium directly to the large intestine, and thus bypassing the systemic absorption that occurs in the small intestine, the calcium can exert its beneficial effect on this portion of the body.

Vitamin D

An active form of vitamin D, calcitriol has anti-cancer properties. This form of vitamin D can activate vitamin D receptors, which turn genes on and off, preventing cancer from starting. Calcitriol also encourages cells to either adapt to their new organ or commit apoptosis and keeps surface layers of organs intact. Active vitamin D can limit the blood supply to the tumor and reduce the spread of cancer. As discussed above, vitamin D also increases the absorption of calcium into the large intestines which reduces the risk of colorectal cancer.

As discussed above, calcium can be absorbed actively through intestinal cells by binding to a transport protein known as calbindin present in the intestinal epithelial cells (enterocytes). Calbindin is stimulated by the active vitamin D metabolite and may control the rate of absorption of calcium across the enterocytes. The transport of calcium across the enterocyte cytoplasm can control the calcium absorption in the intestine and the presence of calbindin may increases the amount of calcium crossing the cell without raising the free concentration.

Folic Acid (Vitamin B9 or Folate)

Dietary folate can lower the risk of colorectal cancer. Aberrations in DNA methylation may contribute to abnormalities in DNA synthesis and genomic instability. Cancer may arise from DNA damage at a rate in excess of ongoing DNA repair and/or the inappropriate expression of critical genes. Because of the important roles played by folate in DNA and RNA synthesis and methylation, folate can improve both DNA repair and gene expression. Folate is a methyl group donor in the DNA methylation cycle, a byproduct of which is homocysteine. Folate increases DNA methylation in leukocytes and colorectal mucosa and can protect the DNA in cells from cancer-causing substances and may stop tumors from forming in the colon. A lack of folate intake may lead to hypomethylation, which can lead to dysregulation of proto-oncogenes. Folate deficiency can also alter nucleotide precursor pools, causing uracil to be incorporated incorrectly during DNA synthesis. The result is DNA strand breakage and chromosome damage. Folate deficiency may induce mutation by inducing DNA strand breaks in a highly conserved region of the tumor suppressor genes.

Vitamin B2 (Riboflavin)

Folates play potentially important roles in carcinogenesis because of their role as major carriers of the one-carbon groups needed for intracellular methylation reactions and nucleotide synthesis. Folate-associated one-carbon metabolism depends on B-vitamin cofactors for many of the key reactions involved. Thus, methylenetetrahydrofolate reductase requires vitamin B2.

Vitamin B6 (Pyridoxine)

Vitamin B6 can lower the risk of colorectal cancer by preventing abnormalities in DNA synthesis, repair, and methylation. Vitamin B6 is a cofactor in the conversion of methionine to cysteine and is involved in methylation pathways necessary for normal DNA formation, maintenance and repair.

Beta-carotene

Beta-carotene has antineoplastic effects partly because of its antioxidant potency.

Selenium

Selenium can protect colonic cells against a wide range of external and internal stressors. Selenium can also actively inhibit the growth of malignant colonic cells. Different mechanisms have been proposed for the anticarcinogenic effect of selenium, including their abilities to maintain membrane integrity, to protect against oxidative and carcinogen-mediated DNA damage, alterations in carcinogen metabolism, effects on the immune system, production of cytotoxic selenium metabolites with antitumorigenic effects, inhibition of specific enzymes, and stimulation of apoptosis.

Curcumin

Curcumin is the principal curcuminoid of the spice turmeric, which is a member of the ginger family. Curcumin's potential anticancer effects stem from its ability to induce apoptosis in cancer cells without cytotoxic effects on healthy cells. Curcumin can interfere with the activity of the transcription factor NF-κB, which has been linked to a number of inflammatory diseases such as cancer. Curcumin may inhibit mTOR complex I via a novel mechanism. Curcumin may also modulate the growth of tumor cells through regulation of multiple cell signaling pathways including cell proliferation pathway (cyclin D1, c-myc), cell survival pathway (Bcl-2, Bcl-xL, cFLIP, XIAP, c-IAP1), caspase activation pathway (caspase-8, 3, 9), tumor suppressor pathway death receptor pathway (DR4, DR5), mitochondrial pathways, and protein kinase pathway (JNK, Akt, and AMPK)". Curcumin may effectively inhibit tumor cell proliferation, as well as migration and invasion, and that these effects may be mediated through interference with the STAT3 signaling pathway.

Green Tea Extract

Green tea extract is an herbal derivative from green tea leaves (Camellia sinensis) and can contain antioxidant ingredients including green tea catechins (GTC). The anticarcinogenic properties of green tea extracts include inhibitory effects on cancer cells. In in vitro assays, catechin and caffeine, which are main components in green tea extracts, may block the cell cycle of cancer cells (cytotoxicity) and induce programmed cell death. Green tea extracts may also inhibit prostatic carcinoma.

The forms and dosage ranges for ingredients of embodiments in the colon vitamin are listed in Table 1 below.

TABLE 1

| Ingredient | Form | Daily Dosage |
| --- | --- | --- |
| Calcium | Calcium Carbonate (40% elemental calcium) | 50-2,000 mg |
| Vitamin B2 | Riboflavin | 0.25-10 mg |
| Vitamin B6 | Pyridoxine HCl | 0.25-10 mg |
| Folic Acid, Vitamin B9 | pteroylglutamic acid | 25-2,000 mg |
| Vitamin D | Cholecalciferol (Vitamin D$_3$) | 50-3,000 IU |
| Beta-Carotene | Plant oil extracts or other forms | 1-75 mg |
| Selenium | l-selenomethionine | 25-500 mcg |
| Curcumin | Turmeric spice | 5-2600 mg |
| Green Tea Extract | *Camellia sinensis* leaves | 300-400 mg |

The present disclosure, in various embodiments, includes components, methods, processes, systems and/or apparatus substantially as depicted and described herein, including various embodiments, subcombinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation. Rather, as the flowing claims reflect, inventive aspects lie in less than all features of any single foregoing disclosed embodiment.

What is claimed is:

1. A colon vitamin taken by a patient to prevent colorectal adenomatous polyps and colorectal cancer, the colon vitamin comprising:
   a first capsule comprising: a first group of ingredients that includes vitamin D and a first portion elemental calcium, a first polymer surrounding the first group of ingredients, the first polymer layer releasing the first group of ingredients in a stomach or a small intestine of the patient wherein the first polymer is made of a first poly(meth)acrylate and includes a time release mechanism that releases the first group of ingredients within about 30 to 90 minutes ingestion by the patient and wherein the first polymer includes a pH release mechanism that releases the first group of ingredients after exposure to digestive liquids having a pH level of less than 5.0; and
   a second capsule comprising: a second polymer surrounding a second portion of elemental calcium, the second polymer releasing the second portion of elemental calcium in a large intestine of the patient wherein the second polymer is different than the first polymer and made of a second poly(meth)acrylate and wherein the second polymer includes a time release mechanism that releases the second portion of elemental calcium within about 8-20 hours after ingestion by the patient;
   wherein the first capsule and the second capsule are administered in a single dosage form.

2. The colon vitamin of claim 1 wherein the first polymer and the second polymer are separate structures and the colon vitamin is a two-piece structure.

3. The colon vitamin of claim 1 wherein the first group of ingredients includes the vitamin D and one or more of the following: folate, vitamin B2, vitamin B6, selenium, beta-carotene, curcumin, green tea extract, and a portion of the calcium serving.

4. The colon vitamin of claim 1 wherein first polymer layer includes a pH release mechanism that releases the first group of ingredients after exposure to digestive liquids having a pH level of about 6.0 to 7.0.

5. The colon vitamin of claim 1 wherein second polymer layer includes a pH release mechanism that protects the elemental calcium from digestive liquids having a pH level of less than 5.0 and releases the elemental calcium in the digestive liquids having a pH level equal or greater than 7.0.

6. A colon vitamin for preventing colorectal adenomatous polyps and colorectal cancer, the colon vitamin comprising:
   a first capsule comprising: a first delivery portion that includes vitamin D; a first polymer surrounding the first delivery portion, the first polymer releasing the first delivery portion in a stomach or a small intestine of the patient wherein the first polymer is made of a first poly(meth)acrylate and includes a time release mechanism that releases the first delivery portion within about 30 to 90 minutes ingestion by the patient and wherein the first polymer includes a pH release mechanism that releases the first delivery portion after exposure to digestive liquids having a pH level of less than 5.0;
   a second capsule comprising: a second delivery portion that includes calcium and at least one other ingredient; and a second polymer surrounding the second delivery portion, the second polymer releasing the second delivery portion in a large intestine of the patient wherein the second polymer is made of a second poly(meth)acrylate that is different than the first poly(meth)acrylate and wherein the second polymer includes a time release mechanism that releases the second portion of elemental calcium within about 8-20 hours after ingestion by the patient;

wherein the first capsule and the second capsule are administered in a single dosage form.

7. The colon vitamin of claim 6 wherein the first polymer and the second polymer are separate structures and the colon vitamin is a two piece structure.

8. The colon vitamin of claim 6 wherein the first group of ingredients includes one or more of the following: folate, vitamin B2, vitamin B6, selenium, beta-carotene, curcumin, green tea extract, and a portion of the calcium serving.

9. The colon vitamin of claim 6 wherein first polymer includes a pH release mechanism that releases the first group of ingredients after exposure to digestive liquids having a pH level of 6.0 to 7.0.

10. The colon vitamin of claim 6 wherein second polymer includes a pH release mechanism that protects the second delivery portion from digestive liquids having a pH level of less than 5.0 and dissolves in liquids having a pH level equal to or greater than 7.0.

\* \* \* \* \*